US008352568B2

(12) United States Patent
Walker et al.

(10) Patent No.: US 8,352,568 B2
(45) Date of Patent: Jan. 8, 2013

(54) SYSTEM, APPARATUS, METHOD AND COMPUTER PROGRAM PRODUCT FOR CONFIGURING DISPARATE WORKSTATIONS (75) Inventors: Kelly Walker, Raleigh, NC (US); Charles Ashley Leonard, Morrisville, NC (US)

(73) Assignee: McKesson Financial Holdings, Hamilton (BM)

( * ) Notice: Subject to any disclaimer, the term of this patent is extended or adjusted under 35 U.S.C. 154(b) by 131 days.

(21) Appl. No.: 12/119,098

(22) Filed: May 12, 2008

(65) Prior Publication Data

US 2009/0282133 A1 Nov. 12, 2009

(51) Int. Cl.
*G06F 15/167* (2006.01)
(52) U.S. Cl. ............ 709/214; 709/220; 709/221; 710/8; 705/3; 706/3
(58) Field of Classification Search .................. 709/214, 709/220, 221; 705/3
See application file for complete search history.

(56) References Cited

U.S. PATENT DOCUMENTS

| 6,760,755 | B1* | 7/2004 | Brackett | 709/214 |
|---|---|---|---|---|
| 2006/0259654 | A1* | 11/2006 | Shafer | 710/8 |
| 2007/0018120 | A1* | 1/2007 | Beloussov et al. | 250/493.1 |
| 2008/0154957 | A1* | 6/2008 | Taylor et al. | 707/104.1 |
| 2009/0063193 | A1* | 3/2009 | Barton et al. | 705/3 |
| 2009/0088820 | A1* | 4/2009 | Mao et al. | 607/59 |

* cited by examiner

*Primary Examiner* — Kyung H Shin
(74) *Attorney, Agent, or Firm* — Alston & Bird LLP (57) ABSTRACT

A system, apparatus, method and computer program product are provided for configuring disparate workstations. In particular, an administrative utility is provided that may allow users to upload to a configuration server individual configuration files for applications executing on workstations associated with physiological devices. Once uploaded, a user may group the configuration files into configuration groups based, for example, on similarities in configurations utilized. Once a configuration group has been created, the user may assign one or more workstations to each configuration group. Upon startup of a workstation, an application executing on the workstation may automatically transmit a request to the configuration server to load the configurations for that workstation. In response, the configuration server may determine to which configuration group the workstation has been assigned, and then download the configuration files of that configuration group to the workstation. The downloaded configuration files may then control the behavior of the application.

21 Claims, 10 Drawing Sheets

SYSTEM, APPARATUS, METHOD AND COMPUTER PROGRAM PRODUCT FOR CONFIGURING DISPARATE WORKSTATIONS

FIELD

Embodiments of the invention relate, generally, to configuring applications operating on disparate workstations and, in particular, to an improved technique for ensuring that up-to-date configuration settings are applied to each workstation in a convenient and efficient manner.

BACKGROUND

In a hospital, or similar institution, environment multiple physiological devices are often employed to collect various physiological data associated with the patients being cared for at the hospital, or similar institution. These physiological devices may include, for example, anesthesia machines, post anesthesia care units, heart monitors, and/or the like. In many instances, each physiological device may have a workstation associated therewith. The workstation, which may include, for example, a personal computer (PC), laptop, or similar computing device, may provide an interface between the caregiver (e.g., physician, nurse, etc.) and the physiological device. In particular, the workstation may enable the caregiver to enter commands to and receive data from the physiological device and/or generate and output reports based on the data received.

Applications executing on these workstations often require sets of configuration files for controlling the behavior of those applications (e.g., how they interface with the physiological machine, what type of user interface they provide, etc.). An example of such an application may be an anesthesia documentation application executing on a workstation associated with an anesthesia machine.

A different set of configuration files may be required depending upon, among other things, the workstation on which the application is executing, the type or model of the physiological device, the type of institution and/or the department of the institution within which the workstation is operating, and/or the like. Some configuration files may be shared among all workstations within a particular institution (e.g., hospital), whereas others may be workstation, physiological machine and/or department specific.

Currently, in some instances, the configuration files are stored locally on the individual workstations. This may raise issues when a configuration file is modified or updated. In particular, when the configuration files are stored locally on the workstations, each time a configuration file needs to be modified or updated, the configuration file stored locally on each workstation would likely need to be individually, and manually, updated to reflect the modification.

In other instances, in addition to being stored locally on the workstations, a version of one or more of the configuration files may be stored on a central server or similar computing system. In this instance, in order to update a configuration file, modifications may be made to the centrally located version alone. However, in order to update the configuration files stored locally on each workstation, it may be necessary to manually request that the updated configuration files be pushed to the workstations. In addition, currently, not all configuration files are capable of being pushed, and those that are, often are not pushed successfully.

A need, therefore, exists for an improved technique for providing and updating configuration files used to control applications executing on a workstation operating in association with a physiological device or machine.

BRIEF SUMMARY

In general, embodiments of the present invention provide an improvement by, among other things, providing an administrative utility that may allow users to upload, to a central server or similar network entity (referred to as a "configuration server"), individual configuration files associated with applications executing on various workstations that operate in association with physiological devices. Once uploaded, a user may group the configuration files into configuration groups based, for example, on similarities in the configurations utilized. For example, a configuration group may be associated with each of a plurality of different types and/or models of physiological devices. Alternatively, or in addition, a configuration group may, for example, be associated with each of a plurality of different departments in an institution in which the workstations are operated. Once a configuration group has been created, the user may assign one or more workstations to each configuration group. In other words, the user may identify the workstations that should use the configuration files of each configuration group.

Upon startup of a workstation, an application executing on the workstation may automatically transmit a request to the configuration server to load the configurations (i.e., download the configuration files) for that workstation. In response, the configuration server may determine to which configuration group the workstation has been assigned, and then download the configuration files of that configuration group to the workstation. The downloaded configuration files may then control the behavior of the application.

In accordance with one aspect, a system is provided for configuring disparate workstations. In one embodiment, the system may include a physiological device configured to collect and monitor physiological data associated with a patient, a workstation in electronic communication with the physiological device, and a network entity in electronic communication with the workstation. The workstation may be configured to automatically transmit, and the network entity may be configured to receive, a request for one or more configuration files associated with an application executing on the workstation. In response to receiving the request, the network entity may be further configured to retrieve one or more configuration files associated with the workstation, and to transmit the retrieved configuration files to the workstation.

In accordance with another aspect, an apparatus is provided for configuring disparate workstations. In one embodiment, the apparatus may include a processor configured to: (1) receive, from a workstation, a request for one or more configuration files associated with an application executing on the workstation; (2) retrieve one or more configuration files associated with the workstation, in response to the request; and (3) transmit the one or more retrieved configuration files to the workstation.

According to yet another aspect, a method is provided for configuring disparate workstations. In one embodiment, the method may include: (1) receiving, from a workstation, a request for one or more configuration files associated with an application executing on the workstation; (2) retrieving one or more configuration files associated with the workstation, in response to the request; and (3) transmitting the one or more retrieved configuration files to the workstation.

According to another aspect, a computer program product is provided for configuring disparate workstations. The computer program product contains at least one computer-readable storage medium having computer-readable program code portions stored therein. The computer-readable program code portions of one embodiment may include: (1) a first executable portion for receiving, from a workstation, a request for one or more configuration files associated with an application executing on the workstation; (2) a second executable portion for retrieving one or more configuration files associated with the workstation, in response to the request; and (3) a third executable portion for transmitting the one or more retrieved configuration files to the workstation.

In accordance with yet another aspect, an apparatus is provided for configuring disparate workstations. In one embodiment the apparatus may include a processor configured to: (1) automatically, upon start up of the apparatus, transmit a request for one or more configuration files associated with an application executing on the apparatus; (2) receive, in response to transmitting the request, one or more configuration files; and (3) execute the one or more configuration files received.

BRIEF DESCRIPTION OF THE SEVERAL VIEWS OF THE DRAWING(S)

Having thus described embodiments of the invention in general terms, reference will now be made to the accompanying drawings, which are not necessarily drawn to scale, and wherein:

DETAILED DESCRIPTION

Embodiments of the present invention now will be described more fully hereinafter with reference to the accompanying drawings, in which some, but not all embodiments of the inventions are shown. Indeed, embodiments of the invention may be embodied in many different forms and should not be construed as limited to the embodiments set forth herein; rather, these embodiments are provided so that this disclosure will satisfy applicable legal requirements. Like numbers refer to like elements throughout.

Overview:

In general, embodiments of the present invention provide a system, apparatus, method and computer program product for configuring disparate workstations. In particular, according to one embodiment, a central server or similar network entity (referred to as a "configuration server") may be provided, whereby a user may upload to the configuration server various configuration files that may be utilized in association with one or more applications executing on various workstations operating throughout an institution or facility (e.g., a hospital) in association with different physiological devices (e.g., anesthesia machine, post anesthesia care unit, heart rate monitor, etc.). These configuration files may be utilized to control the behavior of the applications including, for example, providing instructions for interfacing with the corresponding physiological device, generating and outputting information to the user, and/or the like.

Once the user has uploaded the configuration files, according to one embodiment, the user may group the configuration files into one or more configuration groups. The groups may be based, for example, on similarities in the configurations utilized by each application. For example, one configuration group may be assembled for all applications operating in association with a certain type or model of an anesthesia machine, while another may be assembled for all applications operating in association with a different type or model anesthesia machine, or with a different type of physiological device altogether. In a similar fashion, once a configuration group has been created, the user may assign one or more workstations to each configuration group depending upon the particular configurations utilized by that workstation. In other words, the user may identify the workstations that should use the configuration files of each configuration group.

In one embodiment, each time a particular application is launched on a workstation, the application may automatically transmit a request to the configuration server to load the configurations (i.e., download the configuration files) for the workstation and, in particular, for that application. In response, the configuration server may determine to which configuration group the workstation has been assigned, and then download the configuration files of that configuration group to the workstation. The downloaded configuration files may then control the behavior of the application.

Figure 1:
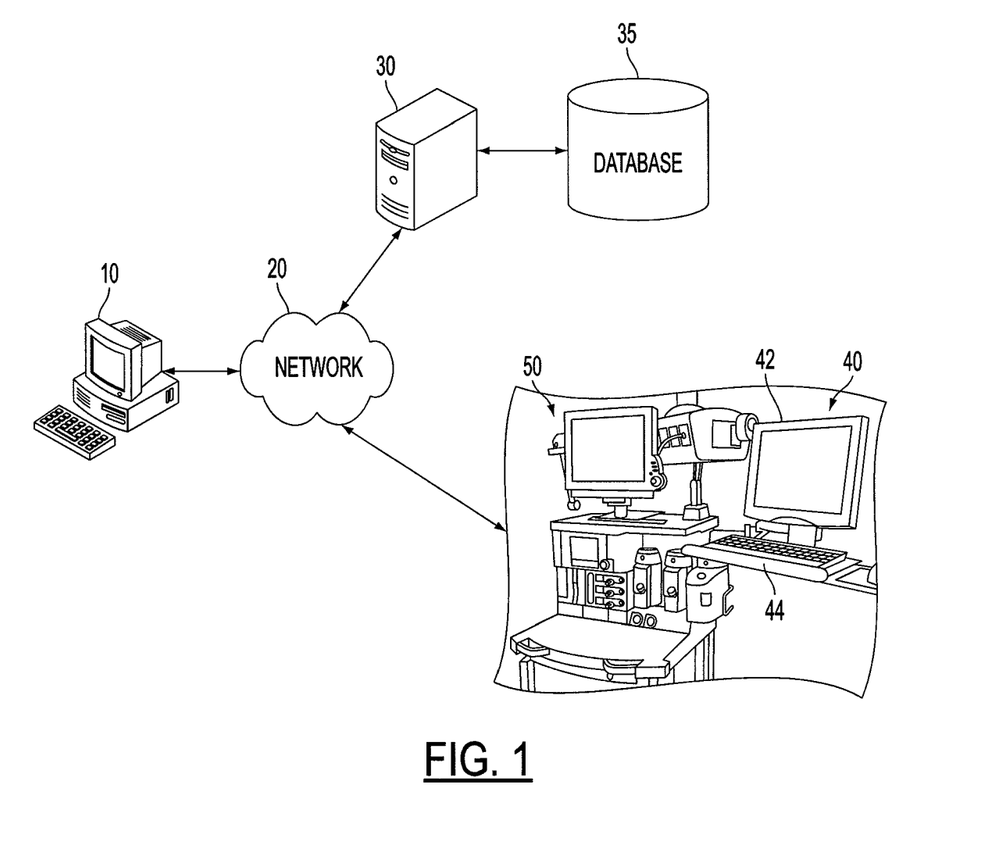
FIG. 1 is a block diagram of one type of system that may benefit from embodiments of the present invention.

Overall System and Configuration Server:

Referring to FIG. 1, an illustration of one type of system that may benefit from embodiments of the present invention is provided. As shown in FIG. 1, the system may include a computing device 10 in communication with a configuration server 30 (an example of which is discussed in more detail below with regard to FIG. 2) over a communication network 20 for the purpose of transmitting one or more configuration files to the configuration server 30. The system may further include a database 35 in electronic communication with the configuration server 30 that stores the configuration files transmitted by the computing device 10.

In particular, according to one embodiment, the computing device may comprise a personal computer (PC), laptop, or similar electronic device, operated by a user for the purpose of creating and/or modifying configuration files and uploading those configuration files to the configuration server 30. The computing device 10 may further be operated by the user for the purpose of transmitting, to the configuration server 30, a designation of one or more configuration groups associated with the uploaded configuration files, as well as a designation of one or more workstations assigned to each configuration group. According to one embodiment, the database 35 may store the configuration files mapped to their corresponding configuration groups, which are further mapped to their corresponding assigned workstations.

The communication network 20 may comprise any wired or wireless communication network including, for example, a wired or wireless personal area network (PAN), local area network (LAN), or wide area network (WAN). As one of ordinary skill in the art will recognize, while the foregoing refers to a configuration "server" 10, embodiments of the present invention are not limited to a client-server relationship or architecture. Embodiments are further not limited to a single server, or similar network entity. In contrast, as one of ordinary skill in the art will recognize, the functionality described herein in association with the configuration server 30 may be shared by multiple servers, or similar network entities, operating in association with one another. In addition, while FIG. 1 illustrates the database 35 as a separate entity from the configuration server 30, as one of ordinary skill in the art will recognize, the database 35 need not be a separate entity and may, instead, be part of the configuration server 30.

According to one embodiment, the system may further include a workstation 40 operating in association with a physiological device or machine 50, such as an anesthesia machine, post anesthesia care unit, heart rate monitor, or the like. In particular, the workstation 40, an example of which is described in more detail below with regard to FIG. 2, may comprise a personal computer (PC), laptop, or similar computing device having a monitor 42, keyboard 44 and/or similar input/output devices used to receive commands from the caregiver for operating the physiological device 50 and to generate outputs, such as reports, or the like, based on data collected by the physiological device 50. According to one embodiment, the workstation 40 may store a number of applications which, when executed, serve to interface with and control the corresponding physiological device 50 (e.g., send commands, monitor outputs, generate reports, etc.).

As described in more detail below, according to one embodiment, the workstation 40 may be in communication with the configuration server 30 over the same or different communication network 20 for the purpose of requesting and receiving one or more configuration files that may be utilized to control the behavior of at least one of the applications being executed on the workstation 40.

Figure 2:
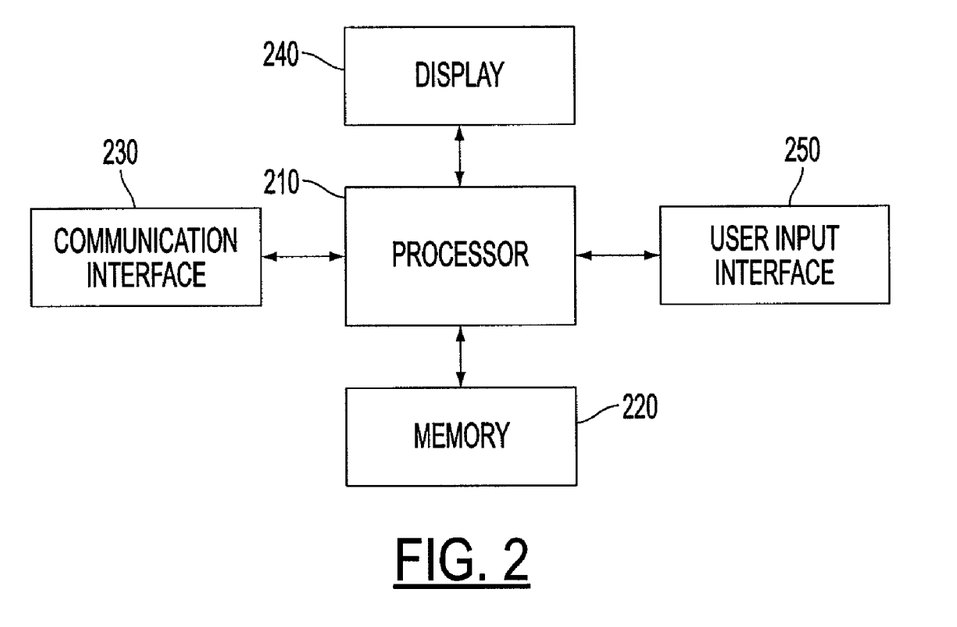
FIG. 2 is a schematic block diagram of an entity capable of operating as a configuration server, or similar network entity, in accordance with embodiments of the present invention.

Referring now to FIG. 2, a block diagram of an entity capable of operating as a configuration server 30 and/or a workstation 40 is shown in accordance with one embodiment of the present invention. The entity capable of operating as a configuration server 30 and/or a workstation 40 may include various means for performing one or more functions in accordance with embodiments of the present invention, including those more particularly shown and described herein. It should be understood, however, that one or more of the entities may include alternative means for performing one or more like functions, without departing from the spirit and scope of the present invention. As shown, the entity capable of operating as a configuration server 30 and/or a workstation 40 can generally include means, such as a processor 210 for performing or controlling the various functions of the entity.

In particular, the processor 210 may be configured to perform the processes discussed in more detail below with regard to FIG. 3 for configuring disparate workstations. For example, according to one embodiment wherein the entity is operating as the configuration server 30, the processor 210 may be configured to receive, from the workstation 40, a request for one or more configuration files associated with an application executing on the workstation. The processor 210 may be further configured to retrieve, in response to the request, one or more configuration files associated with the workstation 40 (e.g., from the database 35); and to transmit the one or more retrieved configuration files to the workstation 40. Alternatively, wherein the entity is operating as the workstation 40, the processor 210 may be configured to automatically (e.g., upon start up of the workstation 40) transmit a request for one or more configuration files associated with an application executing on the workstation 40. The processor 210 may further be configured to receive, in response to transmitting the request, one or more configuration files, and to execute the one or more configuration files received.

In one embodiment, the processor may be in communication with or include memory 220, such as volatile and/or non-volatile memory that stores content, data or the like. For example, the memory 220 may store content transmitted from, and/or received by, the entity. Also for example, the memory 220 (e.g., a memory device that is not transitory) may store software applications, instructions or the like for the processor to perform steps associated with operation of the entity in accordance with embodiments of the present invention. In particular, the memory 220 (e.g., a computer readable storage medium may store software applications, instructions or the like for the processor to perform the operations described above and below with regard to FIG. 3 for configuring disparate workstations.

For example, according to one embodiment wherein the entity is operating as the configuration server 30, the memory 220 may store one or more modules for instructing the processor 210 to perform the operations including, for example, a receive request module, a retrieve module and a transmit configurations module. In one embodiment, the receive request module may be configured to receive the request from the workstation 40 for one or more configuration files associated with an application executing on the workstation 40. The retrieve module may be configured to retrieve, in response to receiving the request, one or more configuration files associated with the workstation 40. Finally, the transmit module may be configured to transmit the one or more retrieved configuration files to the workstation 40. Similarly, where the entity is operating as the workstation 40, the memory 220 may store a transmit request module, a receive configurations module and an execute configurations module. In one embodiment, the transmit request module may be configured to automatically (e.g., upon start up of the workstation 40) transmit a request for one or more configuration files associated with an application executing on the workstation 40. The receive configurations module may be configured to receive, in response to transmitting the request, one or more configuration files. Finally, the execute configurations module may be configured to execute the one or more configuration files received.

In addition to the memory 220, the processor 210 can also be connected to at least one interface or other means for displaying, transmitting and/or receiving data, content or the like. In this regard, the interface(s) can include at least one communication interface 230 or other means for transmitting and/or receiving data, content or the like. For example, where the entity is operating as the workstation 40, the communication interface 230 may be configured to transmit and receive data to and from the physiological device 50 associated with the workstation 40. The interface(s) may further include at least one user interface that can include a display 240 (e.g., the workstation monitor 42) and/or a user input interface 250. The user input interface, in turn, can comprise any of a number of devices allowing the entity to receive data from a user, such as a keypad (e.g., the workstation keypad 44), a touch display, a joystick or other input device.

Method of Configuring Disparate Workstations

Figure 3:
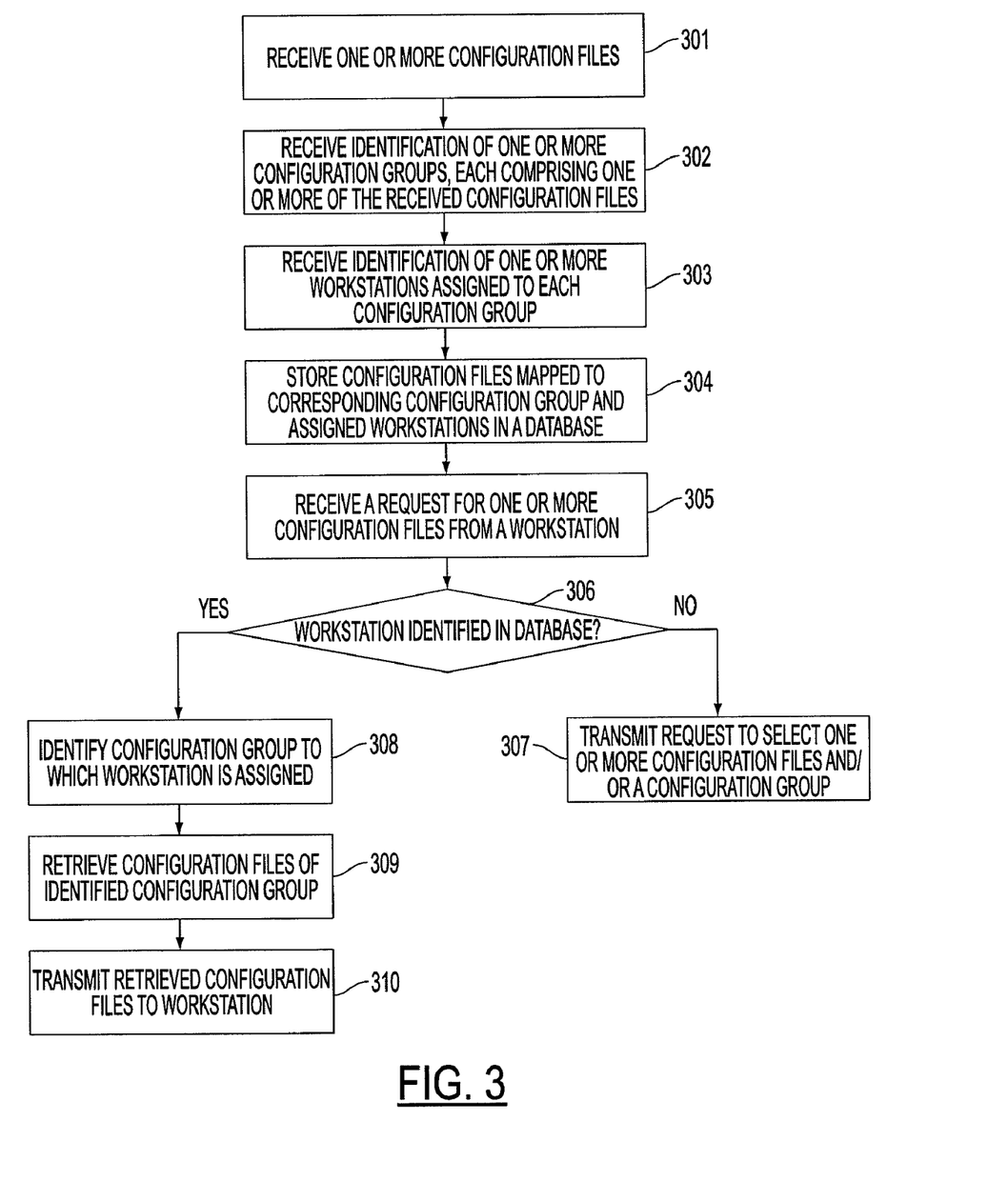
FIG. 3 is a flow chart illustrating the process of automatically pulling configuration files in accordance with embodiments of the present invention.

Referring now to FIG. 3, the operations are illustrated that may be taken in order to configure disparate workstations in accordance with an embodiment of the present invention. As shown, the process may begin at Block 301, where a configuration server, or similar network entity, (e.g., means, such as a processor operating on the configuration server, or similar network entity) receives one or more configuration files, for example, from a computing device (e.g., personal computer (PC), laptop, etc.) operated by a user (e.g., a caregiver, hospital administrator, etc.). As discussed above, the configuration files may be associated with applications being executed on various workstations operating throughout a hospital, or similar institution, in association with different physiological devices (e.g., anesthesia devices, post anesthesia care units, heart monitors, etc.). The configuration files, which may comprise text documents capable of being encoded in Extensible Markup Language (XML), Comma Separated Variable (CSV), HyperText Markup Language (HTML), or plain text, may define, or control, various aspects of these applications including, for example, the interface between the application/workstation and the corresponding physiological device, the user interface provided (e.g., fields included in the interface and how displayed and/or populated), the manner of outputting documents to a backend records system, and/or the like.

Figure 4A:
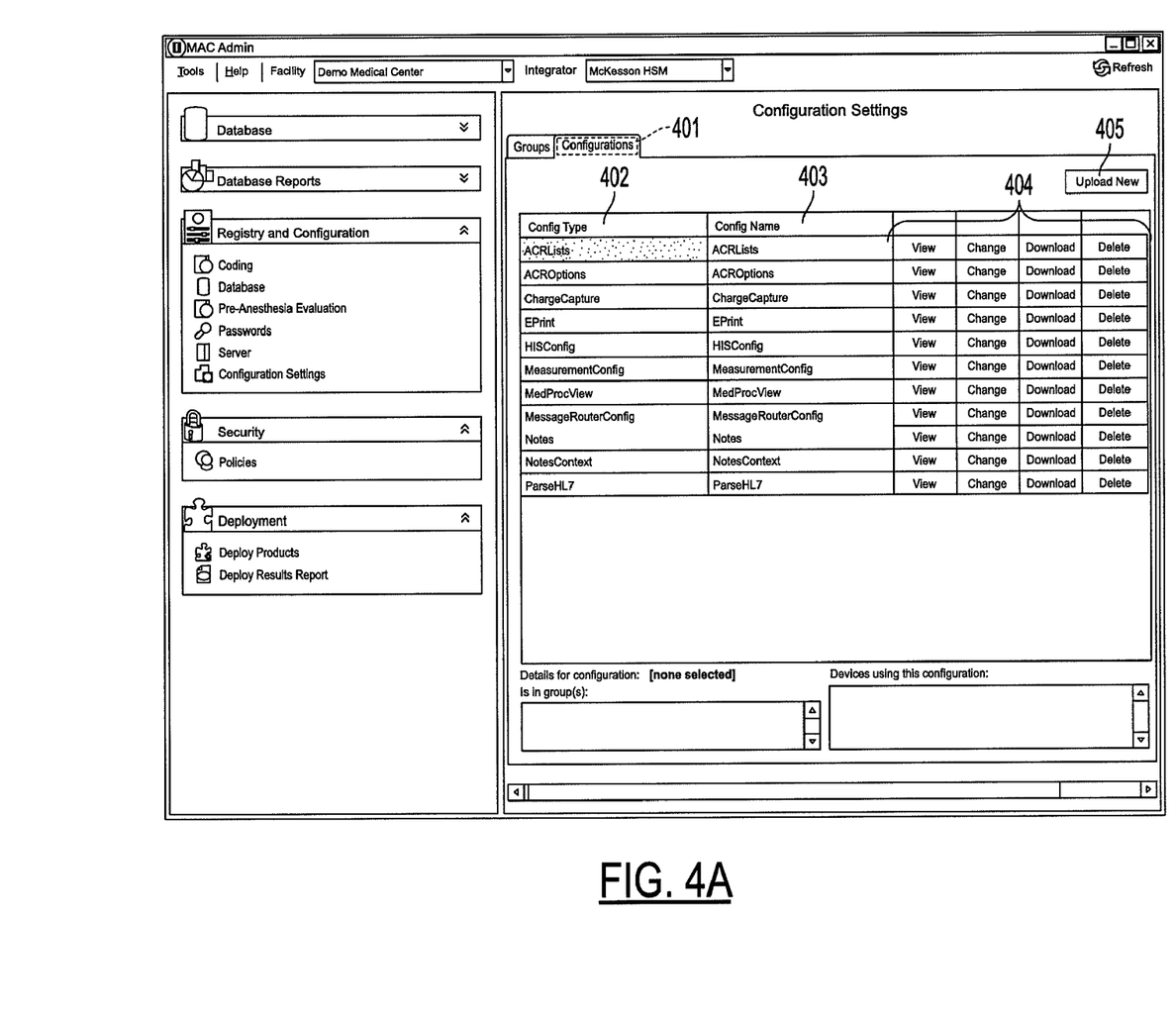
FIGS. 4A-4E illustrate an example of a user interface that may be used to upload configuration files to the configuration server in accordance with an embodiment of the present invention.

FIGS. 4A through 4E provide an example of a user interface that may be provided by the computing device for uploading the configuration files to the configuration server. In particular, as shown in FIG. 4A, the "Configurations" tab 401 of the user interface may include a Configuration Type 402 list including a listing of all of the types of configuration files that may be uploaded to the configuration server. For example, assuming that the configuration files being uploaded are associated with an anesthesia documentation application executed on a workstation operating in association with an anesthesia device or post anesthesia care unit, the types of configuration files that may be uploaded may include, for example, configuration files that define how various controls are displayed and/or behave (e.g., the ACRLists Configuration Type), what and to where documents should be printed (e.g., the Eprint Configuration Type), different physiological mappings to be generated (e.g., the MeasurementConfig Configuration Type) and/or the like. Once a configuration file associated with a particular configuration type has been uploaded, the name of the uploaded configuration file may be displayed in the Configuration Name 403 list also provided by the user interface. The user interface may further provide selectable tabs 404 for viewing, changing, downloading and deleting the uploaded configuration files of each type.

Figure 4B:
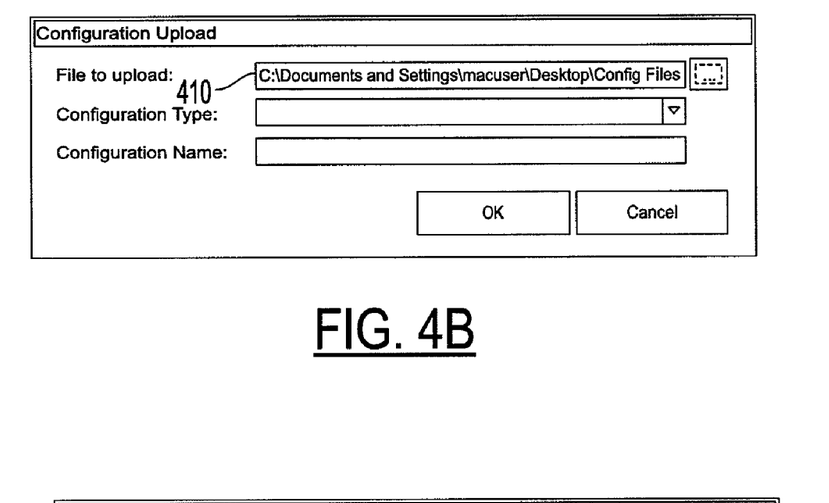
Figure 4C:
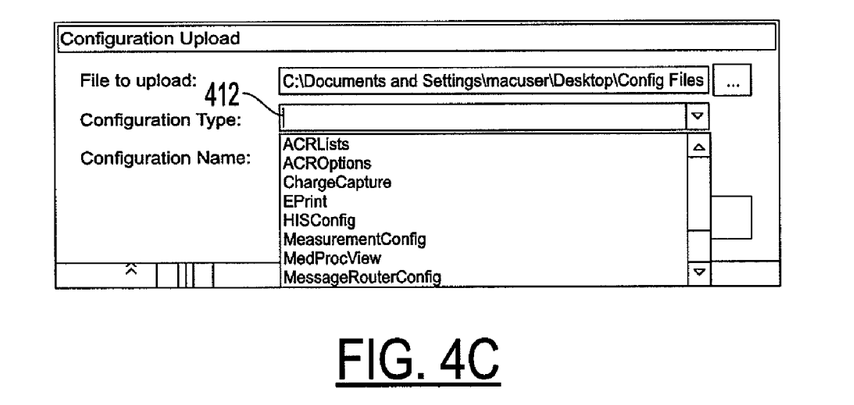
Figure 4D:
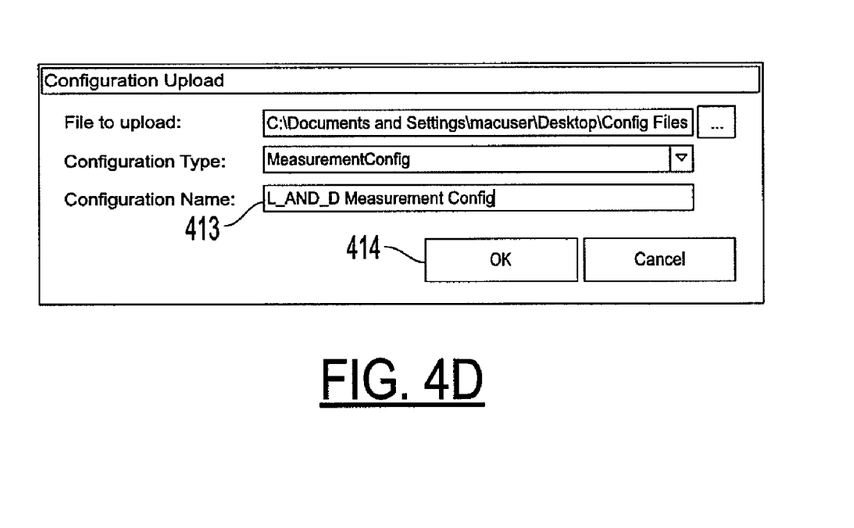
Figure 4E:
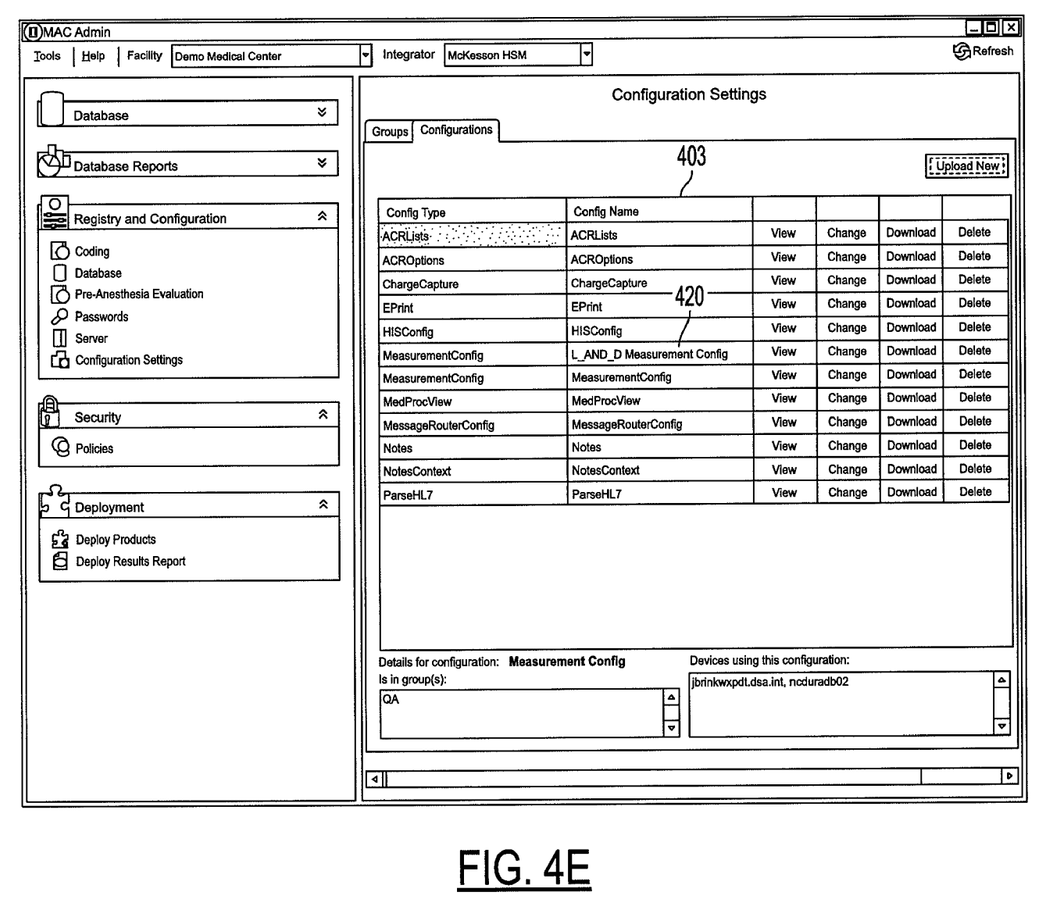

According to one embodiment, when a user wishes to upload a configuration file of a particular type, he or she may press the "Upload New" selection button 405 displayed by the user interface. Upon selection, a screen similar to the one shown in FIGS. 4B-4C may be provided. Using this screen, the user may first select the configuration file to upload to the configuration server (e.g., from memory on the computing device) by browsing to the location of the configuration file (shown in FIG. 4B). Once the configuration file has been selected, the originating address or location of the configuration file may be displayed in a "File to Upload" field 410 on the display screen. The user may then select the configuration type associated with the uploaded configuration file, for example using a drop down menu (shown in FIG. 4C). The selected configuration type may likewise be displayed in a "Configuration Type" field 412 on the display screen. Finally, the user may input a name for the uploaded configuration file, which may be displayed in a "Configuration Name" field 413 of the display screen (shown in FIG. 4D). Once the configuration file has been selected, assigned to an appropriate configuration type and named, the user may select an "OK" tab 414, causing the configuration file 420 to be uploaded and added to the list of uploaded configuration files 403, as shown in FIG. 4E.

Returning to FIG. 3, after a user has uploaded the configuration files to the configuration server, the server (e.g., means, such as a processor) may, at Block 302, receive an identification of one or more configuration groups, each comprising one or more of the uploaded configuration files. In particular, according to one embodiment of the present invention, the user may define one or more configuration groups in which the uploaded configuration files should fall, for example, using a user interface like the own shown in FIGS. 5A-5D. According to one embodiment, groups may be defined based on various combinations of factors associated with the applications controlled by the configuration files, the workstations on which those applications are executed and/or the physiological devices associated with those workstations.

For example, according to one embodiment, different configuration groups may be defined for configuration files to be used for applications executing on workstations associated with different types and/or models of physiological devices. Alternatively, or in addition, different configuration groups may be defined for configuration files to be used for applications executing on workstations operating in different institutions and/or different departments within an institution. Different configuration groups may likewise be defined for configuration files that provide different user preferences for different aspects of the application. As one of ordinary skill in the art will recognize, the foregoing are just a few examples of how configuration files may be grouped in order to provide different configuration settings. Other, similar, factors and methods may likewise be used without departing from the spirit and scope of embodiments of the present invention.

Figure 5A:
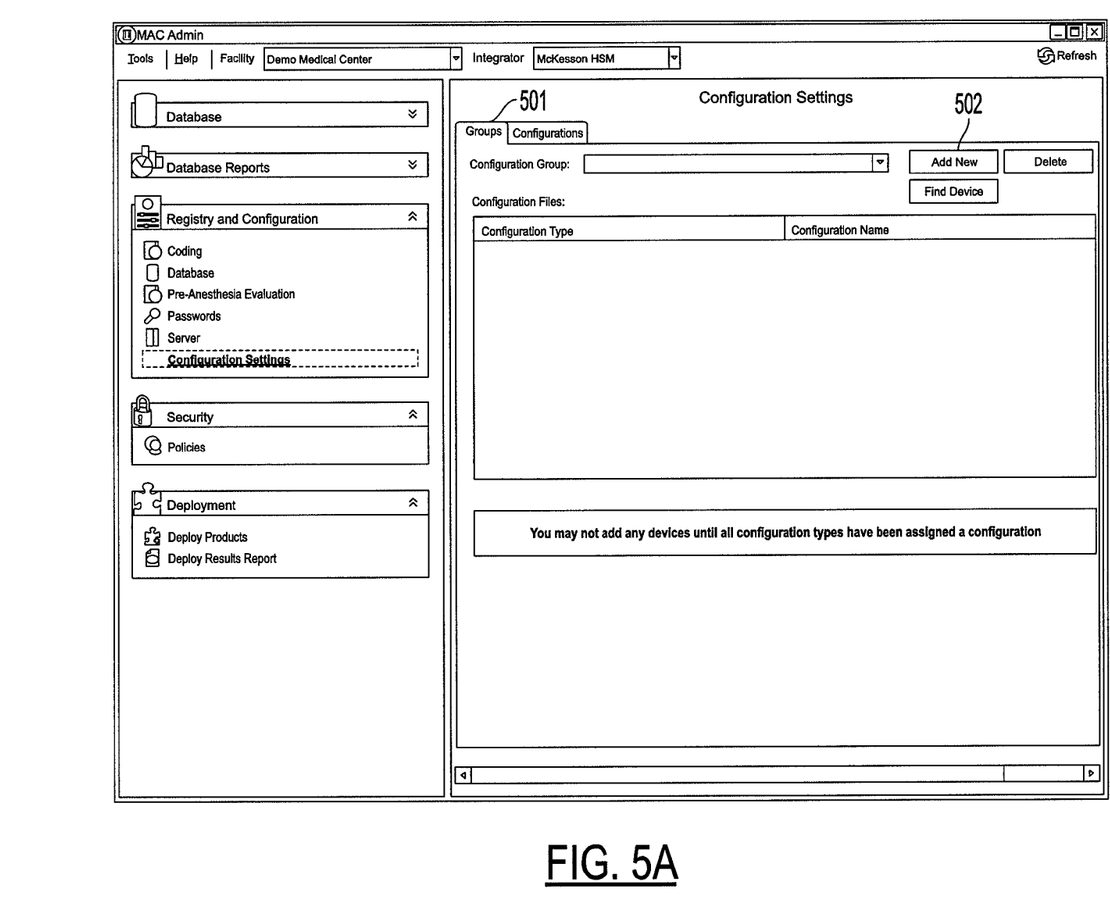
FIGS. 5A-5D illustrate an example of a user interface that may be used to define a configuration group in accordance with an embodiment of the present invention.

Referring now to FIGS. 5A-5D, according to one embodiment, when the user wishes to define a configuration group including one or more of the previously uploaded configuration files, he or she may first select, from the "Groups" tab 501 of the user interface, the "Add New" selection button 502 (as shown in FIG. 5A). Upon selection, a screen similar to one shown in FIG. 5B may be provided, wherein the user can input the name of the configuration group 510 and select the "OK" button 512. Using a screen similar to that shown in FIGS. 5C and 5D, the user may then select uploaded configuration files for each configuration type to be included in the configuration group. For example, upon selection, a drop down menu 520 may be provided for each configuration type, from which the user may select from configuration files uploaded in association with that configuration type. Once the configuration file has been selected, the name of the selected configuration file may be displayed in the Configuration Name list 521 next to the corresponding configuration type in the Configuration Type list 522.

Figures 6A, 6B:
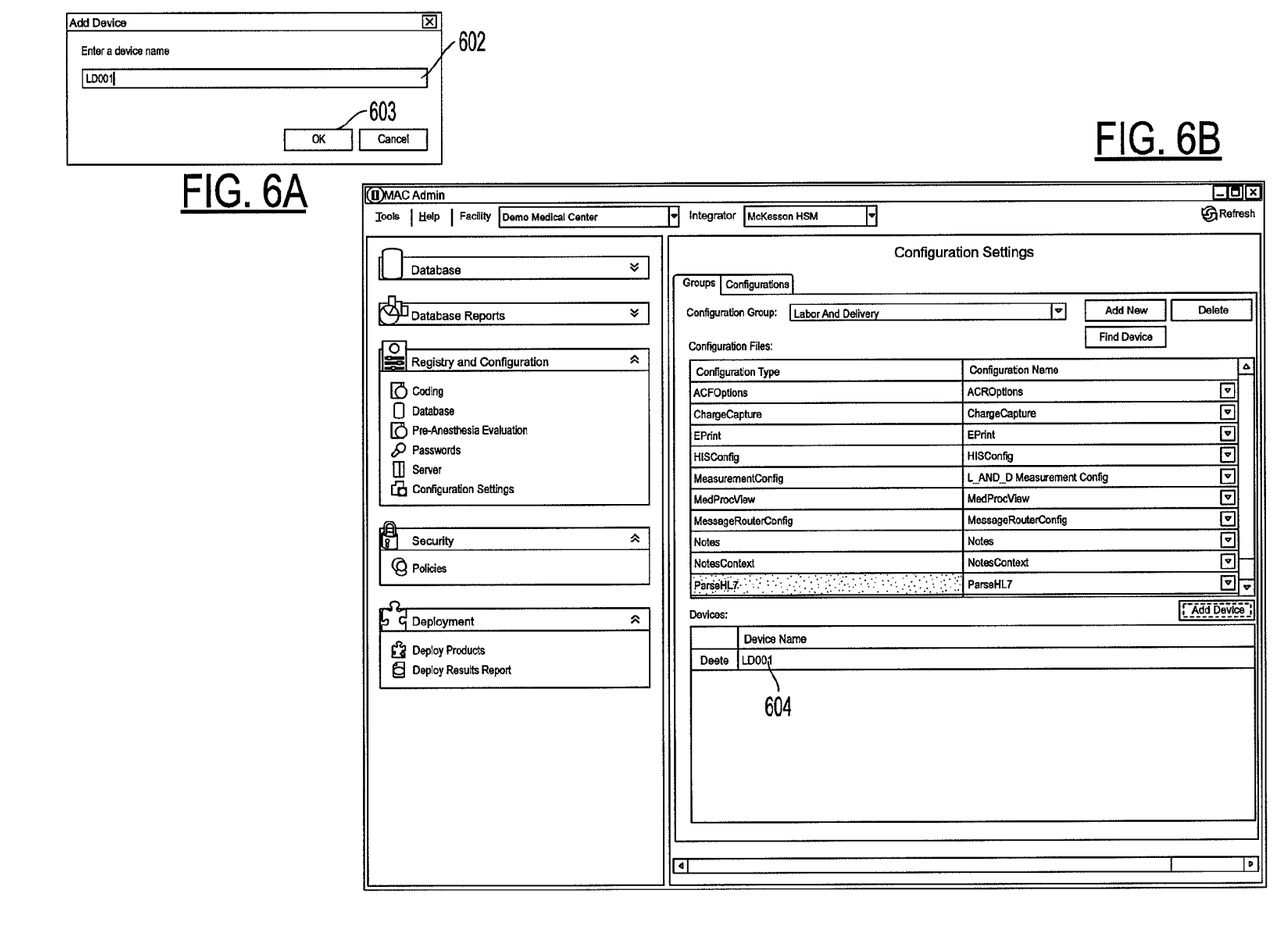
FIGS. 6A-6B illustrate an example of a user interface that may be used to assign one or more workstations to a configuration group in accordance with an embodiment of the present invention.

Once the user has defined the various configuration groups in which each of the configuration files may fall, he or she may then assign one or more workstations to the respective configuration groups. In particular, the user's computing device may provide a user interface like the one shown in FIGS. 6A and 6B to enable the user to identify the workstations assigned to each configuration group, and the configuration server (e.g., means, such as a processor) may, at Block 303, receive the identification from the computing device. Workstations may be assigned to different configuration groups based on similar factors and in similar manners as configuration files were assigned to different configuration groups. For example, workstations associated with different models and/or types of physiological devices may be assigned to different configuration groups. Workstations operating in different institutions and/or in different departments within those institutions may likewise be assigned to different configuration groups. Similarly, workstations operated by different users having different preferences may be assigned to different configuration groups. In other words, according to embodiments of the present invention, a particular workstation may be assigned to a particular configuration group based, among other things, on the physiological device associated with the workstation, the workstation itself (e.g., its location), a user associated with the workstation and/or the application executing on the workstation.

Figures 5B, 5C:
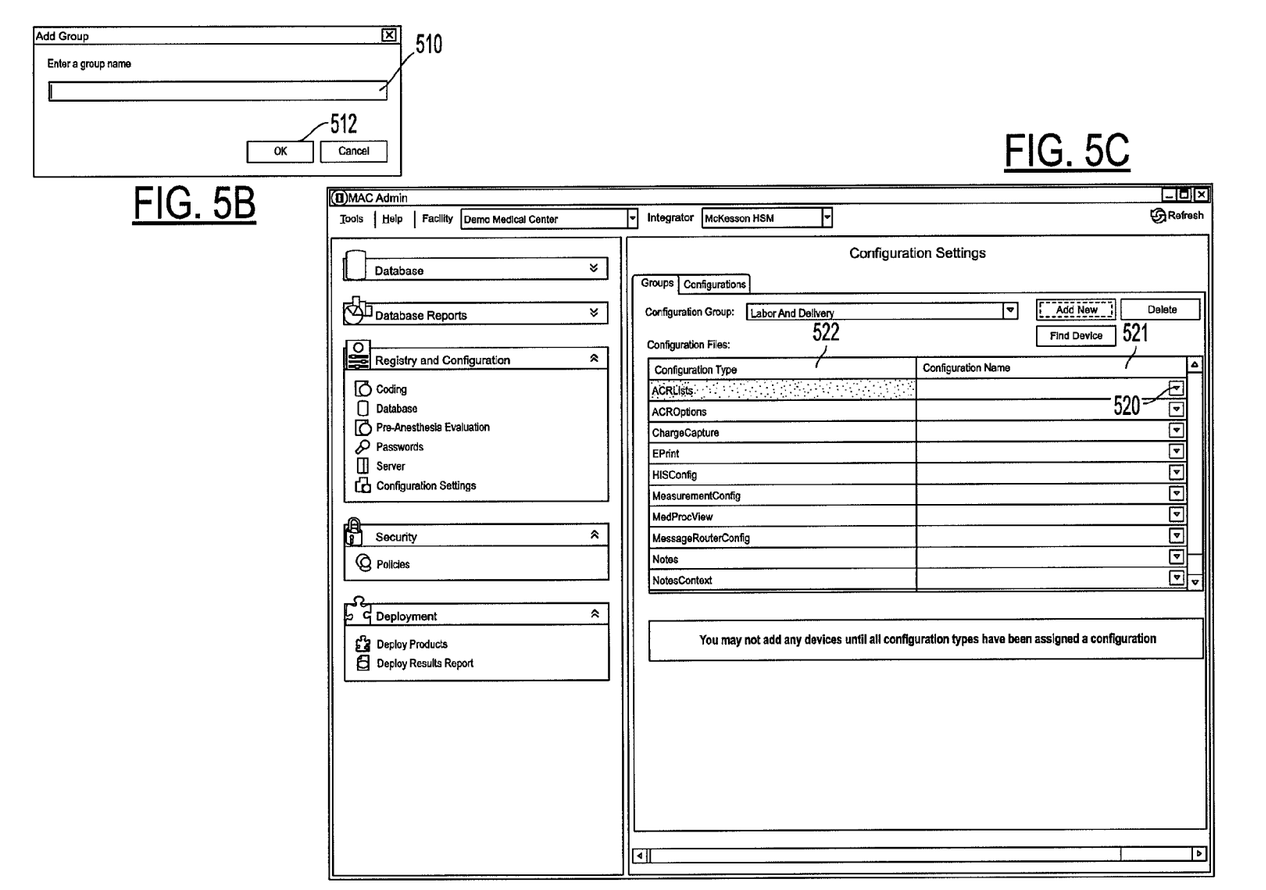
Figure 5D:
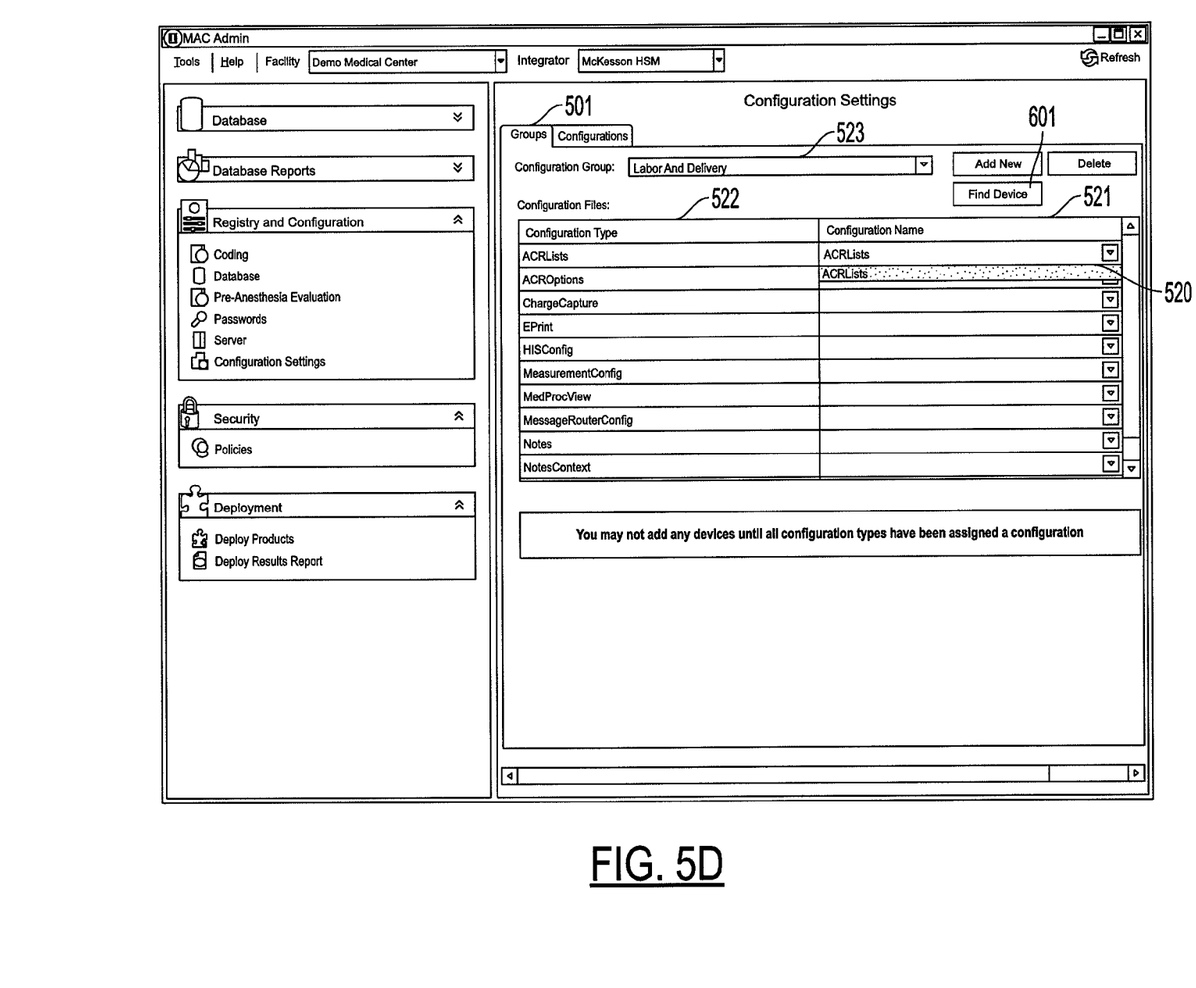

Referring to FIGS. 5A through 6B, according to one embodiment, when the user wishes to assign a workstation to a particular configuration group, he or she may do so by first selecting the "Find Device" button 601 from the "Groups" tab 501 associated with the desired configuration group 523 (shown in FIG. 5B). Upon selection, a screen like the one shown in FIG. 6A may be displayed, wherein the user may input the name of the device 602 he or she would like to assign to the configuration group and then select the "OK" button 603. In response to the user selecting the "OK" button 603, the device identified may be added to the list of devices 604 associated with the configuration group (shown in FIG. 6B). The user may repeat this process as many times as needed to assign all of the desired workstations to each of the configuration groups.

The configuration server (e.g., means, such as a processor) may, at Block 304, store the uploaded configuration files, for example on a database, wherein the files may be mapped to the corresponding configuration groups, and the configuration groups may be similarly mapped to the assigned workstations.

At some point thereafter, a user (e.g., a caregiver, such as a nurse, physician, etc.) may log on to his or her workstation and launch one of the applications executing on the workstation. According to one embodiment, when this occurs, the application may automatically transmit a request to the configuration server for the configuration files associated with the workstation and that application. The configuration server (e.g., means, such as a processor and, in one embodiment, the receive request module) may receive this request at Block 305.

Upon receiving the request for configuration files, the configuration server (e.g., means, such as a processor) may, at Block 306, first determine whether the workstation is identified within the database among the workstations that have been assigned to a particular configuration group. If not, the configuration server (e.g., means, such as a processor) may, at Block 307, transmit a request to the workstation to select one or more configuration files and/or a configuration group to be downloaded. In one embodiment, the workstation may display this request to the user for him or her to identify the appropriate configurations for the workstation.

If, on the other hand, it is determined at Block 306, that the workstation is identified within the database among the workstations that have been assigned to a particular configuration group, the configuration server (e.g., means, such as a processor and, in one embodiment, the retrieve module) may first identify the configuration group to which the workstation has been assigned (at Block 308), retrieve the configuration files of the identified configuration group (at Block 309), and then transmit the retrieved configuration files to the workstation (at Block 310). The workstation (e.g., the application executing on the workstation) may thereafter execute the configuration files received, such that the behavior of the application executing on the workstation may be controlled by the downloaded configuration files.

CONCLUSION

As described above and as will be appreciated by one skilled in the art, embodiments of the present invention may be configured as a system, apparatus or method. Accordingly, embodiments of the present invention may be comprised of various means including entirely of hardware, entirely of software, or any combination of software and hardware. Furthermore, embodiments of the present invention may take the form of a computer program product on a computer-readable storage medium having computer-readable program instructions (e.g., computer software) embodied in the storage medium. Any suitable computer-readable storage medium may be utilized including hard disks, CD-ROMs, optical storage devices, or magnetic storage devices.

Embodiments of the present invention have been described above with reference to block diagrams and flowchart illustrations of methods, apparatuses (i.e., systems) and computer program products. It will be understood that each block of the block diagrams and flowchart illustrations, and combinations of blocks in the block diagrams and flowchart illustrations, respectively, can be implemented by various means including computer program instructions. These computer program instructions may be loaded onto a general purpose computer, special purpose computer, or other programmable data processing apparatus, such as processor 210 discussed above with reference to FIG. 2, to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus (e.g., processor 210 of FIG. 2) to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Many modifications and other embodiments of the inventions set forth herein will come to mind to one skilled in the art to which these embodiments of the invention pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A system comprising:
a physiological device configured to collect and monitor physiological data associated with a patient;
a workstation in electronic communication with the physiological device, said workstation configured to automatically transmit a request for one or more configuration files associated with an application executing on the workstation; and
a network entity in electronic communication with the workstation, said network entity comprising a memory and a processor configured to:
receive, from a computing device, an indication of a plurality of configuration groups that are each assigned to comprise one or more of a plurality of received configuration files;
receive, from the computing device, an indication of a plurality of workstations that are each assigned to one of the plurality of configuration groups;
generate a mapping of respective configuration files of the plurality of received configuration files and respective workstations of the plurality of workstations to a corresponding configuration group of the plurality of configuration groups based on the indications received;
receive the request;
determine that the workstation is assigned to one of the plurality of configuration groups by accessing the mapping;
retrieve at least one of the plurality of configuration files associated with the configuration group to which the workstation is assigned, in response to the request; and
transmit the at least one retrieved configuration file to the workstation.

2. The system of claim 1, wherein the physiological device is selected from a group consisting of an anesthesia machine, a post anesthesia care unit and a heart rate monitor.

3. The system of claim 1, wherein the application comprises a documentation application configured to receive the physiological data collected by the physiological device and to generate and output one or more reports based on the physiological data received.

4. The system of claim 1 further comprising:
a database storing the one or more configuration files, respective configuration files mapped to the corresponding configuration group and to the plurality of workstations assigned to the configuration group.

5. The system of claim 4, wherein the network entity is further configured to:
access the database and retrieve the at least one configuration file associated with the determined configuration group to which the workstation is assigned.

6. The system of claim 1, wherein the at least one configuration group is based in part on a type or model of the physiological device.

7. An apparatus comprising:
a processor and a memory comprising computer software, which when executed by the processor causes the apparatus to:
receive, from a computing device, an indication of a plurality of configuration groups that are each assigned to comprise one or more of a plurality of received configuration files;
receive, from the computing device, an indication of a plurality of workstations that are each assigned to one of the plurality of configuration groups;
receive, from a workstation, a request for one or more configuration files associated with an application executing on the workstation;
generate a mapping of respective configuration files of the plurality of received configuration files and respective workstations of the plurality of workstations to a corresponding configuration group of the plurality of configuration groups based on the indications received;
determine that the workstation is assigned to one of the plurality of configuration groups by accessing the mapping;
retrieve at least one configuration file associated with the configuration group to which the workstation is assigned, in response to the request; and
transmit the at least one retrieved configuration file to the workstation.

8. The apparatus of claim 7, wherein the memory and the computer software are further configured to, when executed by the processor, cause the apparatus to:
store respective configuration files in a database mapped to the corresponding configuration group and the plurality of workstations assigned to the configuration group.

9. The apparatus of claim 8, wherein, in order to retrieve one or more configuration files, the memory and the computer software are further configured to, when executed by the processor, cause the apparatus to:
retrieve, from the database, the at least one configuration file associated with the determined configuration group to which the workstation is assigned.

10. The apparatus of claim 7, wherein the workstation is associated with a physiological device configured to collect and monitor physiological data associated with a patient.

11. The apparatus of claim 10, wherein the application comprises a documentation application configured to receive the physiological data collected by the physiological device and to generate and output one or more reports based on the physiological data received.

12. The apparatus of claim 7, wherein the request is received automatically upon startup of the workstation.

13. A method comprising:
receiving, from a computing device, an indication of a plurality of configuration groups that are each assigned to comprise one or more of a plurality of received configuration files;
receiving, from the computing device, an indication of a plurality of workstations that are each assigned to one of the plurality of configuration groups;
receiving, from a workstation, a request for one or more configuration files associated with an application executing on the workstation;
generating a mapping of respective configuration files of the plurality of received configuration files and respective workstations of the plurality of workstations to a corresponding configuration group of the plurality of configuration groups based on the indications received;
determining that the workstation is assigned to one of the plurality of configuration groups by accessing the mapping;

retrieving at least one of the plurality of configuration files associated with the configuration group to which the workstation is assigned, in response to the request; and transmitting the at least one retrieved configuration file to the workstation.

14. The method of claim 13 further comprising:
storing respective configuration files in a database mapped to the corresponding configuration group and to the plurality of workstations assigned to the configuration group.

15. The method of claim 14, wherein retrieving one or more configuration files further comprises:
retrieving, from the database, the at least one configuration file associated with the determined configuration group to which the workstation is assigned.

16. The method of claim 13, wherein the workstation is associated with a physiological device configured to collect and monitor physiological data associated with a patient.

17. The method of claim 16, wherein the application comprises a documentation application configured to receive the physiological data collected by the physiological device and to generate and output one or more reports based on the physiological data received.

18. The method of claim 13, wherein receiving the request further comprises receiving the request automatically upon startup of the workstation.

19. A computer program product comprising at least one non-transitory computer-readable storage medium having computer-readable program code portions stored therein, said computer-readable program code portions comprising:
a first executable portion configured to facilitate receipt, from a computing device, of an indication of a plurality of configuration groups that are each assigned to comprise one or more of a plurality of received configuration files;
a second executable portion configured to facilitate receipt, from the computing device, of an indication of a plurality of workstations that are each assigned to one of the plurality of configuration groups;
a third executable portion configured to facilitate receipt, from a workstation, of a request for one or more configuration files associated with an application executing on the workstation;
a fourth executable portion configured to generate a mapping of respective configuration files of the plurality of received configuration files and respective workstations of the plurality of workstations to a corresponding configuration group of the plurality of configuration groups based on the indications received;
a fifth executable portion configured to determine that the workstation is assigned to one of the plurality of configuration groups by accessing the map;
a sixth executable portion configured to retrieve at least one of the plurality of configuration files associated with the configuration group to which the workstation is assigned, in response to the request; and
a seventh executable portion configured to transmit the at least one retrieved configuration file to the workstation.

20. The computer program product of claim 19, wherein the computer-readable program code portions further comprise:
an eighth executable portion configured to facilitate storage of respective configuration files in a database mapped to the corresponding configuration group and to the plurality of workstations assigned to the configuration group.

21. The computer program product of claim 20, wherein the sixth executable portion is further configured to:
retrieve, from the database, the at least one configuration file associated with the determined configuration group to which the workstation is assigned.

* * * * *